United States Patent [19]

Gautier et al.

[11] 4,020,279

[45] Apr. 26, 1977

[54] ADJUSTABLE ANAMORPHIC IMAGE CONVERTER

[75] Inventors: Christian Jean Gautier, Acigne; Jean-Marie Pierre Scarabin, Rennes, both of France

[73] Assignees: L'Etat Francais, represente par le Ministre des Postes et Telecommunications, Issy-les-Moulineaux; Establissement Public dit "Telediffusion de France", Paris; Jean-Marie Pierre Scarabin, Rennes, all of France

[22] Filed: June 16, 1975

[21] Appl. No.: 587,225

[30] Foreign Application Priority Data

June 14, 1974 France .............................. 74.21539

[52] U.S. Cl. ........................ 358/160; 178/DIG. 34
[51] Int. Cl.[2] ........................................ H04N 7/18
[58] Field of Search ............... 178/6, DIG. 34, 2 A, 178/6.8; 350/181

[56] References Cited

UNITED STATES PATENTS 3,485,554   12/1969   Hemstreet .......................... 350/181

*Primary Examiner*—Robert L. Griffin
*Assistant Examiner*—Edward L. Coles
*Attorney, Agent, or Firm*—Laff, Whitesel & Rockman

[57] ABSTRACT

An adjustable anamorphic transformer comprises a source of video signals, which are primarily — but not exclusively — images of a human brain. The video signals have their horizontal and vertical synchronizing signals separated out and then independently processed. The video signals themselves are amplified with an automatic gain control. An electronic means jointly responsive to the separately processed horizontal and vertical signals controls the gain of the video amplifier. Other electronic means separately responsive to the horizontal and vertical signals independently control, in X and Y axes, the expansion of images produced responsive to the video signals.

8 Claims, 5 Drawing Figures

ADJUSTABLE ANAMORPHIC IMAGE CONVERTER

The present invention concerns an adjustable anamorphic transformer of energies, utilising image scanning of the television scanning type and creating from one image an anamorphous variation of the dimensions of selected parts of the image in two directions.

Up till now, special optical means have been used in order to create an anamorphous. For example, concave or convex deforming mirrors, or in the technology of the cinema, special lenses have been used. These means do not permit variation, in actual time, of the parameters of the anamorphic transformation.

It has become evident that an anamorphouses transformation of an image may be achieved by television, with reproduction of the image on a cathode ray tube. To illustrate the possibilities of this technique, certain oscillographs may be cited which, have devices known as electronic lenses which enable a localised variation of the speed of scanning, to produce an expansion of a fraction of the observed signal. However, it must be understood that the object of these systems is not the reproduction of an image; therefore these oscillographs do not constitute anamorphic transformers.

There are various methods of image variation which in television consists of adjusting a certain region of the image, either in a zone of the image, as seen on a different scale, or in another image. However, this method does not realise an anamorphic transformation, because the part of the reproduced picture which would be located under the adjusted part is suppressed. On the other hand, this method necessitates a use of two cameras.

One object of the present invention comprises providing an adjustable anamorphic transformer of images, or more particularly of slides, which are analyzed by a television camera, the output signals of which are transmitted through the transformer to be viewed on a cathode screen directly in the size of a standardized card.

Another object of the present invention resides in providing an adjustable anamorphic transformer for varying the speeds of scanning of the slide or of the visual image, either at the time of taking the view or at the time of visualisation, the changes of speed capable of occuring at selected instance of the periods of scanning.

According to one feature of the invention there is provided an adjustable anamorphic transformer of images comprising means for varying, between two consecutive instances of a period of horizontal and/or vertical scanning of the camera or visualisation tube, the slope of the saw toothed wave applied on the horizontal or vertical deflection plates of the electronics scanning tube or restitution of the image.

According to another feature, the means comprises for each horizontal or vertical scanning, a saw toothed generator, the outlet of which is connected in parallel to a plurality of saw tooth treatment chains. Each chain comprises a direct current amplifier having an adjustable threshold. The output of the amplifier is connected on the one hand to a non-inverting amplifier of unity gain, and on the other hand, to an inverting amplifier of unity gain, the respective outputs of which are connected to the two ends of a potentiometer. The movable slide of the potentiometer is connected to the output of the chain, the outputs of the chains being connected to a circuit of adders. The output of the adder is connected to horizontal or vertical deflection plates of the electronic scanning tube or restitution of image. According to another feature, the output of the circuit of adders is connected to a derivator circuit, the output of which is connected to the input of automatic control of gain of a video amplifier mounted in the video circuit of the view taking or visualisation apparatus.

According to another feature, the output of the D.C. amplifier of each saw tooth treatment chain is connected to the starting input of a mono-stable circuit, the output of which is connected to the input of automatic control of said video amplifier.

In the course of the description which follows, it will be convenient to make reference to the anamorphic transformation of a neuro-radiological stereotaxis slides of the head. However, it must be well understood that the present invention also has other applications which will be mentioned later. As regards the utilization of the neuro-radiological stereotaxis slides, reference may be usefully made to the work entitled "Atlas of Stereotaxis Anatomy of the Telencephalon" by J. Talairach and collaborators, published by Masson and Cie 1967. More particularly, see the definition of a system of telensephalie marking by proportional squaring centered on the base line CA–CP and its verticals. The line CA–CP has invariances which have been made evident by J. Talairach. The line which passes through two points is easy to recognize on radio graphic images because they are the upper edge of the front commissure and the lower edge of the rear commissure.

A squaring, corresponding respectively to profile and face slides, are shown in FIGS. 1 and 2. One distinguishes there, the face line C1–C2 which passes through the points CA and CP, the horizontal line C3–C4, and normal to line C1–C2, the vertical line C5–C6 passing through CA, the vertical line C7–C8 passing through CP and the vertical C9–C10 passing through the points CA–CP which are aligned in the face slide view, FIG. 2. The outer rectangules of the squares have dimensions corresponding to the horizontal and vertical dimensions of the brain, which is the subject of the slide. The lines I and J of the profile and face contours of the brain are respectively tangential to the edges of the rectangles A B C D and E F G H. The lengths A B and D C are equal to C1–C2 and represent the maximum fronto-expatical distance. The widths AD and BC are equal and equal to C5–C6 and C7–C8 and represent the maximum temporal, vertex-lobe distance. The lengths EF and GH are equal and equal to C3–C4 and represent the maximum distance separating the temporal lobes. The width EH and FG are equal to AD.

These rectangles are subdivided by lines parallel to their sides. It will be observed that the surfaces located respectfully above line C1–C2 and line C3–C4 are subdivided into eight bands of equal width while the surfaces located below these lines are subdivided into four bands only. Likewise, the zones situated respectively to the left of line C5–C6 and to the right of line C7–C8 and on both sides of line C9–C10 are divided into four equal vertical bands. The zones between lines C5–C6 annd C7–C8 are not divided.

In another form, it appears that the rectangle of FIG. 1 comprises six zones which are the zone A, C5, CA, C1; the zone C5, C7, CP, CA; the zone C7 B, C2, CP;

the zone C1, CA, C6, D; the zone CA, CP, C8, C6; and the zone C2, C, C8, CP. In FIG. 2, there are two zones E, F, C4, C3; and C3, C4, G, H.

One of the results of the studies in the work already mentioned has been to show that it was possible to define a standardized card of each profile or face slide, although the maximum horizontal and vertical dimensions of the brain vary from one individual to another, as does the distance CA–CP.

The French patent filed on July 30, 1971 under the National Registration No. 71 28002 in the name of J-M Scarabin is for a "Device for squaring the reproductions of an atomocial organ." There is described a device for enabling a superimposing of the optical projections of a profile or face slide of a brain and squaring, such as mentioned. However, this device does not permit a simple and standarized card. In fact, to obtain this card, it is necessary to treat each zone of the slide with relations of similarity varying from one zone to another.

Other features of the present invention will be apparent on reading the following description of one embodiment, the said description being made in relation to the attached drawings, wherein.

Figure 3:
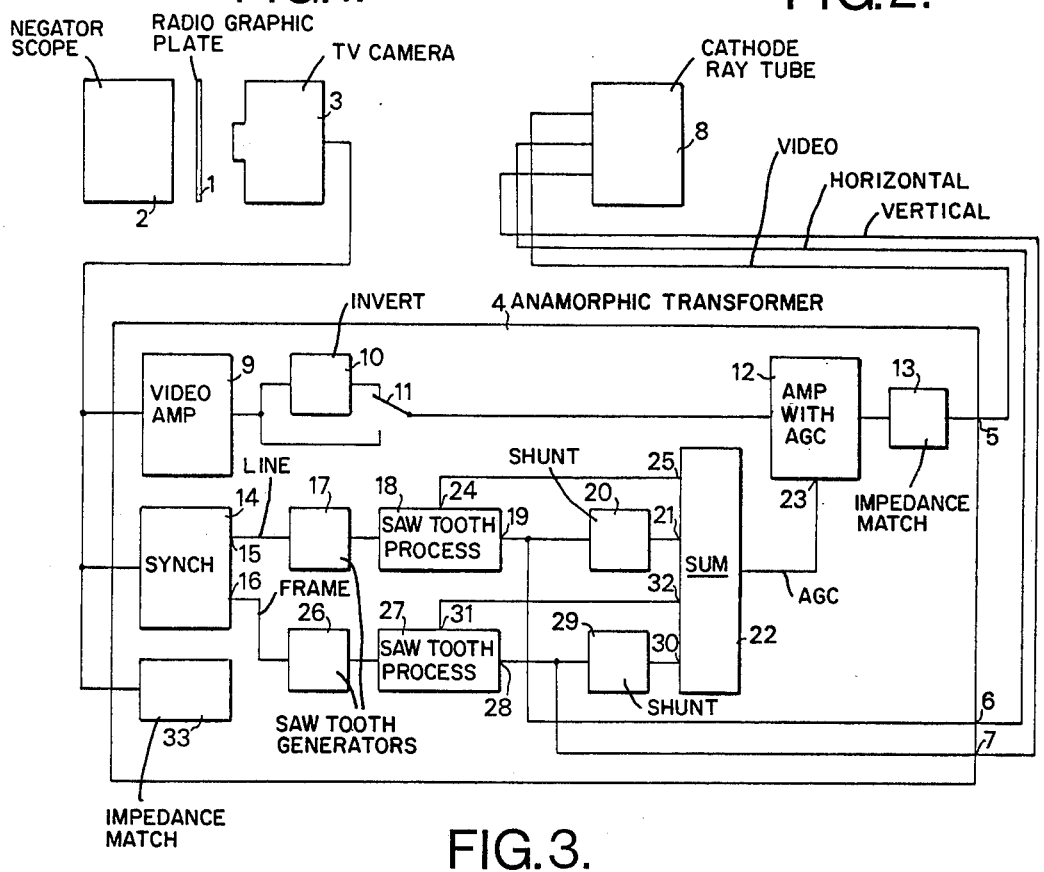
FIG. 3 is a block diagram of an anamorphic transformer according to the invention, associated with a recording apparatus and a viewing apparatus.

In FIG. 3, a radio graphic plate 1 is illuminated by negator scope 2 or any equivalent means, and is analyzed by a conventional television camera 3. The video output of the camera is connected to an anamorphic transformer 4. The transformer 4 has three ouputs 5, 6 and 7 which transmit respectively the video signal, the horizontal deflection voltage and the vertical deflection voltage to the corresponding inputs of a visualisation apparatus comprising cathodic tube 8. The transformer comprises a signal video amplifier 9, the output of which is connected on the one hand to the input of an inverter 10, the output of which is connected to the first fixed contact of a two state switch 11, and on the other hand, the second fixed contact of the switch 11 is connected directly to the output of amplifier 9. The movable contact of 11 is connected to the video input of an amplifier 12, having automatic gain control, the output of which is connected to the input of an impedance adaptor circuit 13. The output 13 is connected to the output 5 for transmitting the video signal to the cathode tube 8.

The transformer comprises also circuit 14 for extraction of synchronization signals and delivers at output 15, line synchronization signals and at its output 16 conventional frame synchronization signals.

The output 15 is connected to the input of a saw-toothed generator 17 comprising a mono-stable circuit and developing saw-tooth horizontal scanning circuiting. The output of 17 is connected to the input of a first saw-tooth processing circuit 18. The output of circuti 18 is connected on the one hand to the output 6 of anamorphic transformer 4, for transmitting the horizontal scanning voltage to the cathode tube 8, and on the other hand to the input of a shunt circuit 20. The output of circuit 20 is connected to the input of 21 of a summing circuit 22 for delivering an automatic gain control signal to the input 23 of the amplifier 12. The circuit 18 has a second output 24 connected to an input 25 of the circuit 22.

The output 16 of the circuit 14 is connected to the input of a saw-tooth generator 26 comprising a monostable circuit and developing vertical scanning saw-tooth circuiting. The output 26 is connected to the input of a second saw-tooth processing circuit 27. The output 28 of circuit 27 is connected on the one hand to the output 7 for transmitting the vertical scanning voltage to the cathode tube 8, and is connected on the other hand to the input of a shunt circuit 29. The output of circuit 29 is connected to the input 30 of the summing circuit 22. The circuit 27 has a second output 31 connected to an input 32 of the circuit 22. Finally, the transformer 4 has also an adaptation impedance 33 terminating the cable connecting it to the output of the camera 3.

Figure 4:
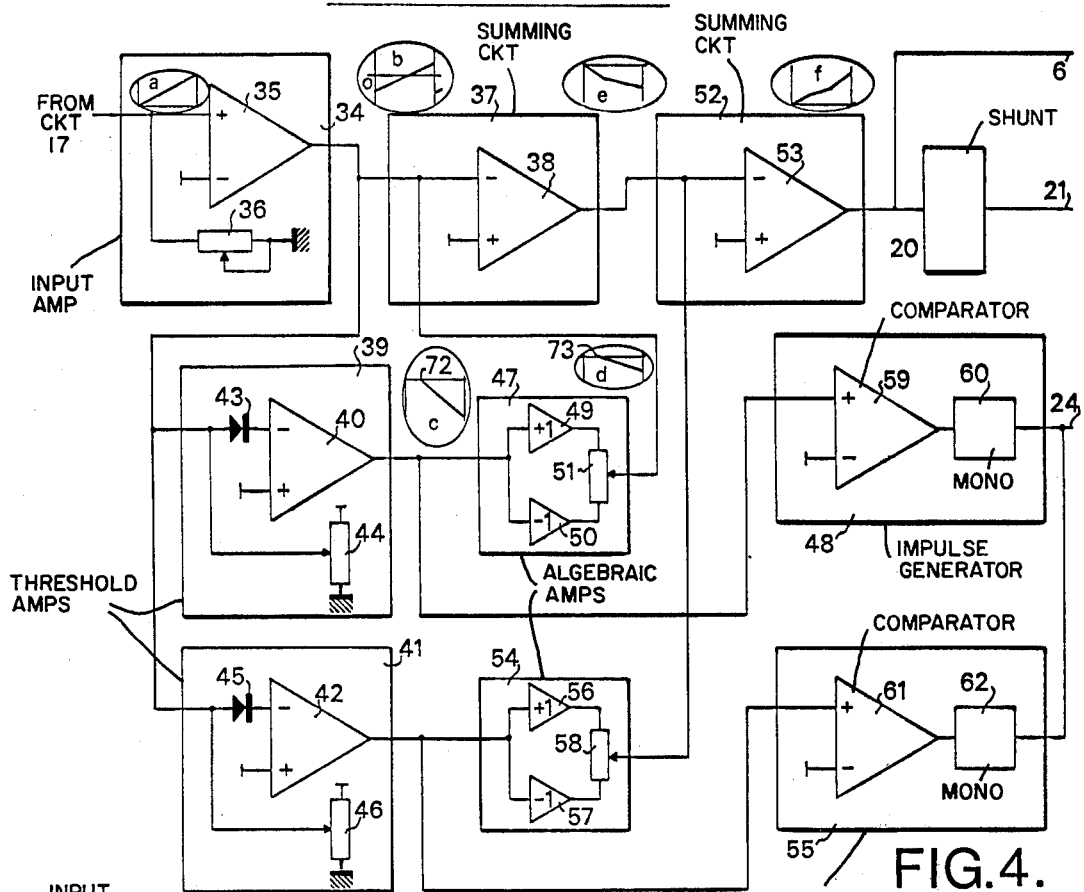
FIG. 4 is an electrical diagram of saw toothed treatment circuits for controlling the horixontal scanning, which are included in the transformer of FIG. 3.

The saw-tooth processing circuit 18 is shown in more detail in FIG. 4. This circuit has an input amplifier 34 mounted as an amplifier antenuator and comprising an operational amplifier 35. The input of amplifier 34 is connected to the output of the horizontal scanning saw-tooth generator 17. The positive input of 35 is likewise connected to a terminal of a resistance of a potentiometer 36 the other terminal of which is connected to the earth. The slide of potentiometer 36 is connected to the earth. The negative input of 35 is connected to a source of polarization voltage.

It must be understood that FIG. 4 does not show the conventional resistances of counter reaction of the amplifier 35 but only the essential parts necessary for comprehension of the functioning of the amplifier. It will be the same as regards the other operational amplifiers of FIGS. 4 and 5. The output of amplifier 35 is connected in parallel to the input of a summer 37 and an operational amplifier 38 and to the input of a threshold amplifier 39 comprising an operational amplifier 40 and at the input of a threshold amplifier 41 comprising an operational amplifier 42.

In amplifier 39 the negative input of the amplifier 40 is connected to the cathode of the diode 43. The anode of diode 43 is connected on the one part to the input of 39 and on the other part to the slide of a potentiometer 44 mounted between the earth and a source of positive voltage. The positive input of amplifier 40 is connected to a source of polarization voltage. Likewise, in amplifier 41, the negative input of the amplifier 42 is connected to the cathode of a diode 45, the anode of which is connected on the one hand to the input of 41 and on the other hand to the slide of amplifier a potentiometer 46 mounted as at 44. The positive input of amplifier 42 is connected to a source of polarization voltage.

The output of amplifier 40 is connected on the one hand to the input of an algebraic amplification circuit 47 and on the other hand to the input of an impulse generator circuit 48. The circuit 47 comprises a non-inverting amplifier 49 of input gain, an inverting amplifier 50 of unit gain, and a potentiometer 51, the terminals of which are effectively connected to the outputs 49 and 50, and the slide of which is connected to the negative input of 38. Amplifiers 49 and 50 may form part of the operational amplifiers. In the summer 37, the negative input of the operational amplifier 38 is thus connected on one hand to the output of amplifier 35 and on the other hand to the slide of potentiometer 51. The positive input of amplifier 38, is connected to a source of polarization voltage. The output of 38 which delivers a total signal of the signal applied to its negative input, is connected to an input of a second summer 52 comprising an operational amplifier 53. The output of 42 is connected on the one hand to the input of an algebraic amplification circuit 54, and on the other hand to the input of an impulse generator circuit 55. The circuit 54 is similar to the circuit 47 and comprises a non-inverting amplifier 56, an inverting amplifier 57 and a potentiometer 58 the slide of which is connected to the negative input of amplifier 53.

In the summer 52, the negative input is connected on the one hand to the output of amplifier 38, and on the other hand to the slide of potentiometer 58. The positive input of amplifier 53 is connected to a source of polarization voltage. The output of amplifier 53, which delivers the total signal of the signals applied to its negative input is connected to on the one hand the output 6 of anamorphic transformer 4 and on the other hand to the shunt circuit 20.

The circuit 48 comprises an operational amplifier 59 mounted as a comparitor and a mono-stable circuit 60, the positive input of 59 is connected to the outlet of amplifier 40 and delivers to the mono-stable circuit 60, each time the voltage of the output of amplifier 40 becomes positive with respect to earth. The mono-stable circuit 60 delivers an output when it is in the working stage a signal to the output 24. The negative input of 59 is connected to earth. The circuit 55 is similar to the circuit 48 and comprises a comparitor amplifier 61 and a mono-stable circuit 62, the output of which is connected to circuit 24. It is to be noted that the time constant of the mono-stable circuit 60 has the same value as the time constant of the mono stable circuit 52 because it defines the width of a vertical marking on the tube 8 as does that of monostable circuit 62. The advantage of these marking will be seen in the description of the functioning of the apparatus.

Figure 5:
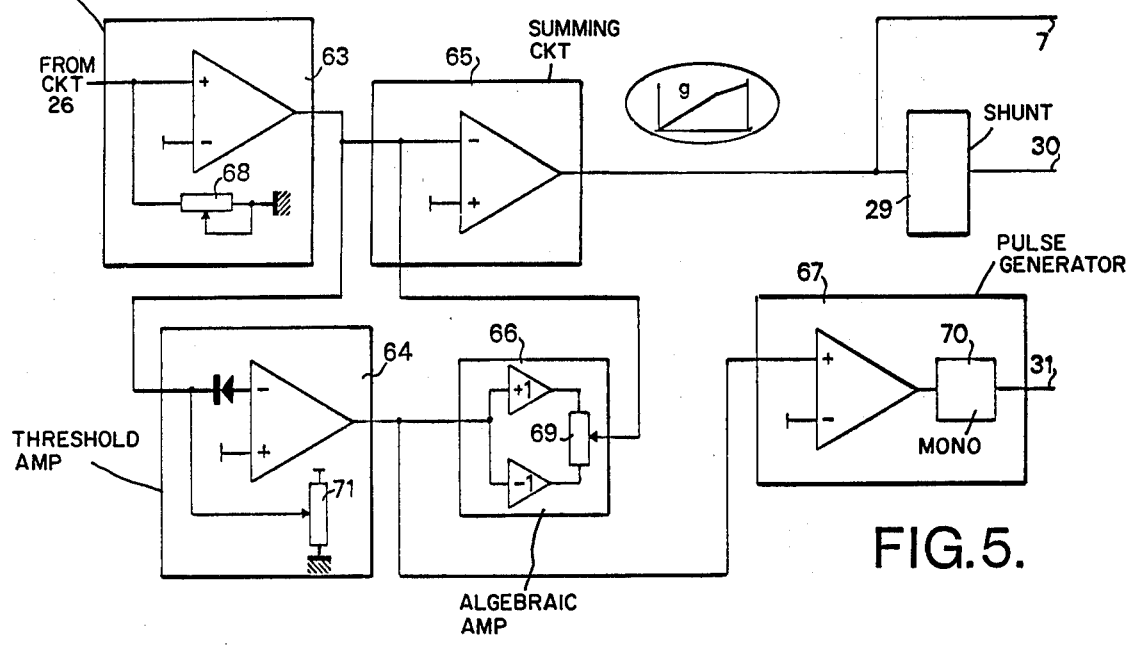
FIG. 5 is an electrical diagram of saw tooth treatment circuits for controlling the vertical scanning which are included in the transformer of FIG. 3.

The saw tooth processing circuit 27 is shown in more detail in FIG. 5. This circuit is constructed with the same elementary circuits as the circuit 18. It comprises an input amplifier 63, identical to amplifier 34 which has its input connected to the output of the vertical scanning of generator 26. The output of amplifier 63 is connected on one hand to the input of the threshold amplifier 64, identical to amplifier 39, and on the other hand to the input of a summer 65, identical with circuit 37; the output of amplifier 64 is connected on the one hand to the input of an algebraic amplifier 66, identical to amplifier 47, and on the other hand, to the input of an impulse generator circuit 67 identical to pulse generator 48. The circuit 63 comprises in particular a potentiometer 68 for permitting or varying the attenuation of the input signal.

The circuit 66 comprises in particular a potentiometer 69 for permitting or varying the signal in the amplitude of the signal applied, by the slide of the potentiometer 69, at the input of the summer 65. The output of summing circuit 65 is connected on the one hand to the output 7 of anamorphic transformer 4 and on the other hand to the input of the shunt circuit 29. The output of the circuit 67 is connected to the output 31. It should be noted that the time constant of the mono-stable circuit 70 or 67 is much greater than that of the mono-stable circuits 60 and 62, because it defines the width of a horizontal marking.

Before describing the complete functioning of the transformer of the invention, the detail functionings of the threshold amplifier 39, the algebraic amplifier 47, the summers 22, and the circuit of FIG. 5, will be described.

It is assumed that the amplifier 38 receives a positive going saw tooth signal such as a shown at its input. It delivers therefore a positive going saw tooth the start of which is relatively negative as shown at $b$, above its input. The saw tooth signal b is combined with the voltage delivered by the slide of the potentiometer 44 and applied to the anode the diode 43 which only allows a signal to pass towards the negative input of amplifier 40 when the amplitude of the saw tooth has reached a value sufficient for the potential at the anode of 43 to be nil or positive. At the output of amplifier 40 one has therefore the signal $c$, shown above this output. It will be seen that the saw tooth signal is delayed in that it starts from point 72. The position of departure 72 is adjustable by adjusting the position of the slide on the potentiometer 44 the control of which is at the decision of the operator.

In the algebraic amplifier 47, the signal $c$ delivered by amplifier 40 is transmited with deformation by amplifier 49 and reversed by amplifier 50. Therefore, at the terminals of potentiometer 51, there are applied respectively symmetrical signals of the same form as $c$. If the slide is in the middle of potentiometer 51, no signal is applied by the slide to the negative input of amplifier 38, which then transmits simply the saw tooth $b$ reversed. If the slide is above the middle of potentiometer 51, it applies to amplifier 38 signal $a$, comprising a negative saw tooth with delayed departure. Then, amplifier 38 transmits the composite broken saw tooth pulse $e$, the first part of which has a steep slope and second a less steep slope. If the slide were below the middle of potentiometer 51, the signal transmitted by amplifier 38 would still be a broken saw tooth, but the slope would increase from a point determined by the position of the slide of potentiometer 44. Summing up, the first point of inclination change of the saw tooth delivered by potentiometer 38 is fixed potentiometer by 44, whilst the variation of slope is fixed by 51. Obviously, the initial slope is fixed the attenuation potentiometer 36.

It will be easily understood that in threshold amplifier 41 and algebraic amplifier 54, the potentiometers 46 and 58 have the same respective functions as potentiometers 44 and 51. The summer 52, similar to summer 37, supplies a saw tooth having two bends and three different slopes. The 44 bend of which has its position determined by potentiometer 46. The variation of the third slope, in respect of the second slope 1 is set by potentiometer 58.

It is likewise easily evident that the broken saw tooth $g$, delivered by summing circuit 65, will have a bend and two slopes fixed respectively by the potentiometer 71 of amplifier 64 and the potentiometers 69 and 68.

The summing circuit 22 (FIG. 3) adds the signals which are transmitted to it at its inputs 25, 21, 32 and 30. It applies at automatic gain control input 23 of the amplifier 12, a voltage such that the gain of the amplifier 12 increases when the sum of the signals which are applied to it increases. Through the input 25, the circuit 12 receives a signal when one of the mono-stable 60 or 62 is in the working state; that is to say when the output of amplifier 40 or of amplifier 42 moves away from zero, (detected by the comparitors 59 or 61), but another may, at instants corresponding to the bends of the curve f. The results on the cathode ray tube 8 is, a brilliant point, at each bend of each scanning line, which produces a brilliant vertical mark. The input 32 of the circuit 22 receives a signal when the mono-stable 70 is in the working state. It will appear to the expert that this signal is expressed on the tube 8 by a horizontal brilliant line.

In addition, it is known that when the slope of the scanning signal is modified there results a modulation of the speed of the spot or a variation of the bases between the lines on the cassored screen. At the input 21, the circuit 22 receives from the shunt circuit 20, a signal which is a function of a derivation of the saw tooth f, that is to say a function of the slope. This signal is stronger, the steeper the slope. That is to say, the speed of the spot is greater. The circuit 22 corrects an increase in speed of the spot, by increasing the gain of amplifier 12; that is to say, the intensity of the signals appearing on the tube 8. Through the input 30, the circuit 22 receives similar signals from the shunt circuit 29.

Figure 1:
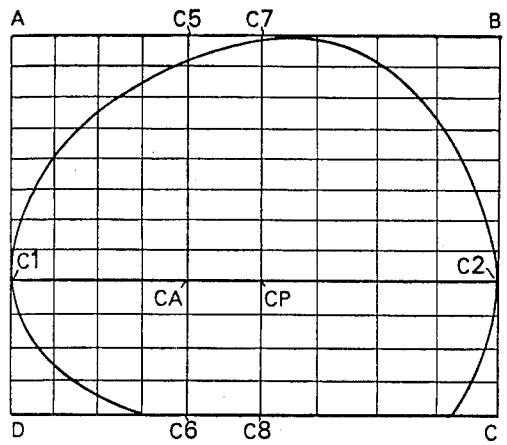
FIG. 1 shows a diagrammatically radiographic profile plate of a brain as well as the squaring of the plate mentioned above.
Figure 2:
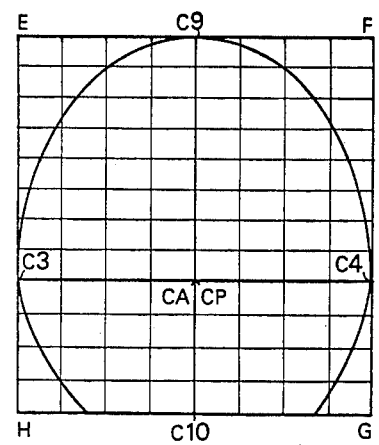
FIG. 2 shows a diagrammatically radiographic face plate of a brain as well as the squaring of the plate mentioned above.

The anamorphic transformer 4, is in a circuit extending between the camera 3 and the tube 8 of FIG. 3. A complete functioning is explained as follows, by taking as an example of application the anamorphoses of a brain plate, such as that symbolised in FIG. 1.

It will be recalled that the anamorphic transformation desired, has the object of deforming the lengths C1. CA, CA–CP etc., so as to obtain a standardised unit from the initial plates. The potentiometers 51, 58 and 69 being in median position, the operator can observe on the screen 8, the undistorted image of screen 1. The operator superimposes on the screen 8 a transparent pattern on which are based the grid lines of FIG. 1 then having marked the front edge of the front commisure of point CA, he operates the potentiometers 36 and 44 so as to create a vertical marking line which he causes to coincide with the lines C5 and C6 of the pattern and bring the edge of the front commisure on this line.

As the action of the potentiometer 36 reacts with the action of potentiometer 44, the operator acts by successive approximation. He then operates potentiometers 51 and 46 in the same manner to bring the second vertical marking line to coincide with the line C-7-C8 of the pattern and to pass through the image points of the lower edge of the rear commisure which he has marked. Then the operator acts on the potentiometer 58 to bring the aceipital part in the line BC of the pattern. The horizontal regulation of the image is then termination. The operator precedes to a similar regulation in the vertical direction by acting on the potentiometer 58, 69 and 71.

In the embodiment described, above it has been considered that the horizontal scanning and the vertical scanning of the camera 3 were antonomous whilst controls of the tube 8 were controlled by the transformer 4. It is obvious that as a variation one can consider a cathode ray tube, the scannings of which are autonomous whilst those of the camera are controlled by the anamorphic transformer. It is sufficient to achieve this to connect the outputs 6 and 7 of the transformer 4 to the respective inputs of the horizontal scanning and vertical scanning controls of the camera 3. This variation may have an advantage when one does not have available a tube 8 with flat screen surface.

It is obvious that the anamorphic transformer of the invention may be used for other applications than medical applications. Thus, in television or the cinema, one may introduce special effects in certain parts of the image and obtain with a variable anamorphous, artistic effects by request. Applications may likewise be be envisaged in teaching.

It should be likewise noted that for each scanning, the number of bends is not limited by considerations of practical order and of cost and may be greater than two.

Although the principles of the present invention have been described above with regard to one particular embodiment, it must be understood that the said description has only been made by way of example and does not limit the scope of the invention.

We claim:

1. In an adjustable anamorphic transformer for images analyzed by a television camera or equivalent, means from transmitting output signals for said camera through said transformer to an image display tube having horizontal and vertical deflection plates, said transformer comprising means for generating saw tooth signals having variable slopes which are between two consecutive points for the horizontal or vertical scannings of the image display tube, comprising means for generating saw tooth signals of fixed slope responsive to synchronization signals taken from signals transmitted by a television camera, a plurality of parallel connected saw tooth processing circuits, means for applying the output of said fixed slope saw tooth generator means to said plurality of saw tooth circuits, each of said processing circuits comprising amplifier means with an adjustable threshold, means for applying the output of said amplifier to a non-inverting current amplifier having gain and to an inverting amplifier of unity gain, means for applying the respective outputs of said non-inverting and said inverting amplifiers to the ends of a potentiometer having a movable slide which is connected to the output of the saw tooth processing circuit, the outputs of the processing circuits being connected to a summing circuit, and means for connecting the output of said summing circuit to horizontal or vertical deflection plates of the image display tube.

2. The transformer according to claim 1 and video amplifier means having automatic gain control, means responsive to the output of the said summing circuit for controlling the automatic gain control of said video amplifier, and means for applying the gain controlled output of said video amplifier to said image display tube.

3. The transformer according to claim 2 wherein in each of said processing circuits includes a monostable circuit means, the output of which is connected to an automatic gain control input of said video amplifier means to increase the gain of the said video amplifier responsive to the output of the said monostable circuit means.

4. An adjustable anamorphic transformer comprising a source of video signals, means for separating horizontal and vertical synchronizing signals from said video signals.

said synchronizing signal processing means comprises means for generating and forming saw tooth wave forms, means for independently processing said separated horizontal and vertical synchronizing signals,
means having gain control for amplifying said video signals,
means jointly responsive to said separately processed horizontal and vertical synchronizing signals for controlling the gain of said video amplifying means, and image display means separately responsive to said processed horizontal and vertical snchronizing signals for independently controlling in X and Y axes the expansion of images produced responsive to said video signals,
said expansion control being responsive to slope and points of inflection of said saw tooth wave forms.

5. The transformer of claim 4 wherein said transformer comprises three channels, a first of said channels comprising a video amplifier driving an amplifier with automatic gain control, the second and third of said channels each comprising a cascade circuit including a saw tooth generator and a saw tooth wave form processing circuit, each saw tooth wave form processing circuit having two outputs, one of said outputs being connected to horizontal and vertical deflection means in an image producing display device and the other of said inputs being connected to a summing circuit, and means responsive to said summing circuit for controlling the automatic gain of said last named amplifier.

6. The transformer of claim 4 and means responsive to said controlled expansion of said image for making uniformly sized and proportioned radiographic images of human brains despite individual variations between the actual sizes and shapes of said brains.

7. The transformer of claim 5 and means responsive to said source of television signals for feeding video signals representing anatomical features into said image display means.

8. The transformer of claim 7 wherein said anatomical feature is a radiographic display of a human brain.

* * * * *

UNITED STATES PATENT AND TRADEMARK OFFICE
CERTIFICATE OF CORRECTION

PATENT NO. : 4,020,279
DATED : April 26, 1977
INVENTOR(S) : Christian Jean Gautier et al.

It is certified that error appears in the above-identified patent and that said Letters Patent are hereby corrected as shown below:

Col. 1, line 27, delete "various"

Col. 2, line 65, "annd" s/b --and--

Col. 4, line 1, "circuti" s/b --circuit--

Col. 4, line 57, --amplifier-- s/b inserted between "of" and "41"

Col. 4, line 58, delete "amplifier"

Col. 5, line 7, --amplifier-- s/b inserted between "of" and "38"

Col. 6, line 46, 1st "potentiometer" s/b --amplifier--; --by-- s/b inserted after "fixed"

Col. 6, line 47, delete "by" at beginning of sentence; insert --potentiometer-- before "51."

UNITED STATES PATENT OFFICE
CERTIFICATE OF CORRECTION

Patent No. 4,020,279  Dated  April 26, 1977

Inventor(s) Christian Jean Gautier et al.  Page 2 of 2

It is certified that error appears in the above-identified patent and that said Letters Patent are hereby corrected as shown below:

Col. 9, line 9, "snchronizing" s/b -- synchronizing --.

Signed and Sealed this ninth Day of August 1977

[SEAL]

Attest:

RUTH C. MASON
Attesting Officer

C. MARSHALL DANN
Commissioner of Patents and Trademark